US00PP07993P

United States Patent [19]

Hesse

[11] Patent Number: Plant 7,993

[45] Date of Patent: Sep. 29, 1992

[54] CHRYSANTHEMUM PLANT NAMED SHELLEY

[75] Inventor: Peter S. Hesse, Nipoma, Calif.

[73] Assignee: Yoder Brothers, Inc., Barberton, Ohio

[21] Appl. No.: 652,418

[22] Filed: Feb. 6, 1991

[51] Int. Cl.[5] ..... A01H 5/00

[52] U.S. Cl. ..... Plt./79

[58] Field of Search ..... Plt./79

*Primary Examiner*—James R. Feyrer

*Attorney, Agent, or Firm*—Foley & Lardner

[57] ABSTRACT

A Chrysanthemum plant named Shelley particularly characterized by its pompon capitulum form; formal decorative capitulum type; light bronze ray floret color with darker center of the flower; diameter across face of capitulum of 38 to 40 mm when fully opened; spreading branching pattern, with 6 to 8 breaks after pinch when grown outside under natural daylength in fall flowerings, and 5 to 7 breaks after pinch when grown in 10 cm pots for spring flowerings; natural season flowering date of September 3 when planting rooted cuttings June 21 in Salinas, Calif., and September 25 to October 1 when planting rooted cuttings June 15 to June 18 in Hightstown, N.J.; flowering response of 55 to 56 days after rooting in no light/no shade programs in spring; plant height of 30 cm when grown in fall under natural daylength with no growth regulators, and 25 cm when grown in 10 cm pots in spring with 1 application of 2500 ppm B-9 SP; and durable, uniform performance.

3 Drawing Sheets

The present invention comprises a new and distinct cultivar of Chrysanthemum, botanically known as *Dendranthema grandiflora*, and referred to by the cultivar name Shelley.

Shelley, identified as 88-#02272, was originated from a cross made by Peter S. Hesse in a controlled breeding program in Parrish, Fla., in 1985.

The female parent of Shelley was the cultivar identified as Sunny Morning, an unpatented variety, and described as a yellow decorative garden mum having a natural season flowering date of August 22 to August 28 in Salinas, Calif., and of October 1 to October 6 in Hightstown, N.J., a flowering response in spring of 49 to 54 days, a height of 25 to 33 cm in fall natural season flowerings, a height of 20 to 25 cm in spring flowerings in 10 cm pots with no growth regulator, and a diameter of capitulum of 70 to 76 mm.

The male parent of Shelley was the cultivar identified as Patriot, disclosed in U.S. Plant Pat. No. 3,897. Based on trials in Salinas, Calif., and in Highstown, N.J., Patriot is a small decorative garden mum, having a white flower color with cream overtones and a light yellow center, a natural season flower date of August 27 to September 3 is Salinas, Calif., and of September 28 to October 1 in Hightstown, N.J., a flowering response in spring of 49 to 59 days, a plant height of 23 to 30 cm in fall natural season flowerings and of 18 to 28 cm in spring flowerings in 10 cm pots with no growth regulators, and a diameter of capitulum of 51 to 57 mm.

Shelley was discovered and selected as one flowering plant within the progeny of the stated cross by Peter S. Hesse in November 1985, in a controlled enviroment in Parrish, Fla.

The first act of asexual reproduction of Shelley was accomplished when vegetative cuttings were taken from the initial selection in January, 1986 in a controlled environment in Parrish, Fla., by technicians working under supervision of Peter S. Hesse.

Horticultural examination of controlled flowerings of successive plantings has shown that the unique combination of characteristics as herein disclosed for Shelley are firmly fixed and are retained through successive generations of asexual reproduction.

Shelley has not been observed under all possible environmental conditions. The phenotype may vary significantly with variations in environment such as temperature, light intensity and daylength.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to basic characteristics of Shelley, which, in combination, distinguish this Chrysanthemum as a new and distinct cultivar:

1. Pompon capitulum form.
2. Formal decorative capitulum type.
3. Light bronze ray floret color with darker center of the flower.
4. Diameter across face of capitulum of 38 to 40 mm when fully opened.
5. Branching pattern is spreading and prolific, with 6 to 8 breaks after pinch when grown outside under natural daylength in fall flowerings, and 5 to 7 breaks after pinch when grown in 10 cm pots for spring flowerings.
6. Natural season flower date of September 3 when planting rooted cuttings and June 21 in Salinas, Calif., and of September 25 to October 1 when planting rooted cuttings June 15 to June 18 in Hightstown, N.J.
7. Flowering response of 55 to 56 days after rooting in no light/no shade programs in spring.
8. Plant height of 30 cm when grown in fall under natural daylength with no growth regulators, and of 25 cm when grown in 10 cm pots in spring with 1 application of 2500 ppm B-9 SP.
9. Durable, uniform performance.

The accompanying photographic drawings show typical inflorescence and leaf characteristics of Shelley, with the colors being as nearly true as possible with illustrations of this type.

Sheet 1 is a color photograph of Shelley grown as a pinched spray pot mum with 4 cuttings in a 15 cm pot.

Sheet 2 is a black and white photograph of three views of the inflorescence of Shelley.

Sheet 3 is a black and white photograph showing the upper and under sides of the leaves of Shelley at 3 stages of development (mature, intermediate and immature).

In sheets 2 and 3 a measuring tape in centimeters has been included.

Of the commercial cultivars known to the inventor, the most similar in comparison to Shelley is the cultivar identified as Mirage, disclosed in U.S. Plant Pat. No. 6,388. Reference is made to attached Chart A, which compares certain characteristics of Shelley to the same characteristics of Mirage.

Similar traits are capitulum form and type, and diameter of capitulum. Shelley has a lighter flower color than Mirage, with a darker center of the flower. In addition, Shelley has an average of one less break per plant, a slower flowering response in all flowering programs, and a greater plant height when compared with Mirage.

When Shelley is compared with both parents, the most striking difference is the diameter of capitulum, which is significantly smaller than that of either parent. In addition, the light bronze flower color with a darker center is not at all expected when crossing parents having yellow and white-cream ray floret color.

In the following description color references are made to The Royal Horticultural Society Colour Chart. The actual color of the ray florets of Shelley is not represented in The R.H.S. Colour Chart, and the values given are those believed closest to the actual color of Shelley. The color values were determined on plant material grown as a pinched spray pot mum in Salinas, Calif. on May 7, 1990.

Classification:

*Botanical.*—*Dendranthema grandiflora* cv Shelley.

*Commercial.*—Pompon formal decorative spray pot mum and garden mum.

INFLORESCENCE

A. Capitulum:

*Form.*—Pompon.

*Type.*—Formal decorative.

*Diameter across face.*—38 to 40 mm when fully opened.

B. Corolla of ray florets:

*Color (general tonality from a distance of three meters).*—Light bronze with a darker center of the flower.

*Color (upper surface).*—17A to 17B, slightly overlaid with 169B to 169C. Center of the flower is stronger overlaid with 169B to 169C.

*Color (under surface).*—17A to 17C.

*Shape.*—Longitudinal, straight. Cross section, concave.

C. Corolla of disc florets: No disc florets present.

D. Reproductive organs:

*Gynoecium.*—Present on ray florets.

PLANT

A. General appearance:

*Height.*—30 cm when grown in fall under natural daylength with no growth regulators, and 25 cm when grown in 10 cm pots in spring with 1 application of 2500 ppm B-9 SP.

*Branching pattern.*—Spreading, with 6 to 8 breaks after pinch when grown outside under natural daylength in fall flowerings, and 5 to 7 breaks after pinch when grown in 10 cm pots for spring flowerings.

B. Foliage:

*Color (upper surface).*—147A.

*Color (under surface).*—147B.

*Shape.*—See photograph.

CHART A

| Characteristic | Shelley | Mirage |
|---|---|---|
| Ray floret color | Light bronze, darker center | Orange bronze |
| Capitulum form and type | Pompon, formal decorative | Pompon, formal |
| Diameter across face of capitulum | 38 to 40 mm | 38 to 41 mm |
| Branching pattern | Spreading | Spreading |
| Breaks, fall outdoors | 6 to 8 | 7 to 9 |
| Breaks, in 10 cm pots | 5 to 7 | 6 to 7 |
| Natural season flower date: | | |
| in Salinas, CA | September 3 | August 21 to 26 |
| in Hightstown, NJ | September 25 to October 1 | September 15 to 21 |
| Flowering response in spring | 55 to 56 days | 45 to 53 days |
| Plant height: | | |
| in natural season fall | 30 cm | 25 to 30 cm |
| in 10 cm pots spring | 25 cm | 20 to 25 cm |

COMPARISONS MADE OF PLANTS GROWN UNDER NATURAL SEASON OUTDOOR CONDITIONS IN SALINAS, CALIFORNIA AND IN HIGHTSTOWN, NEW JERSEY AND IN SPRING FLOWERING PROGRAMS IN SALINAS, CALIFORNIA

I claim:

1. A new and distinct Chrysanthemum plant named Shelley, as described and illustrated.

* * * * *

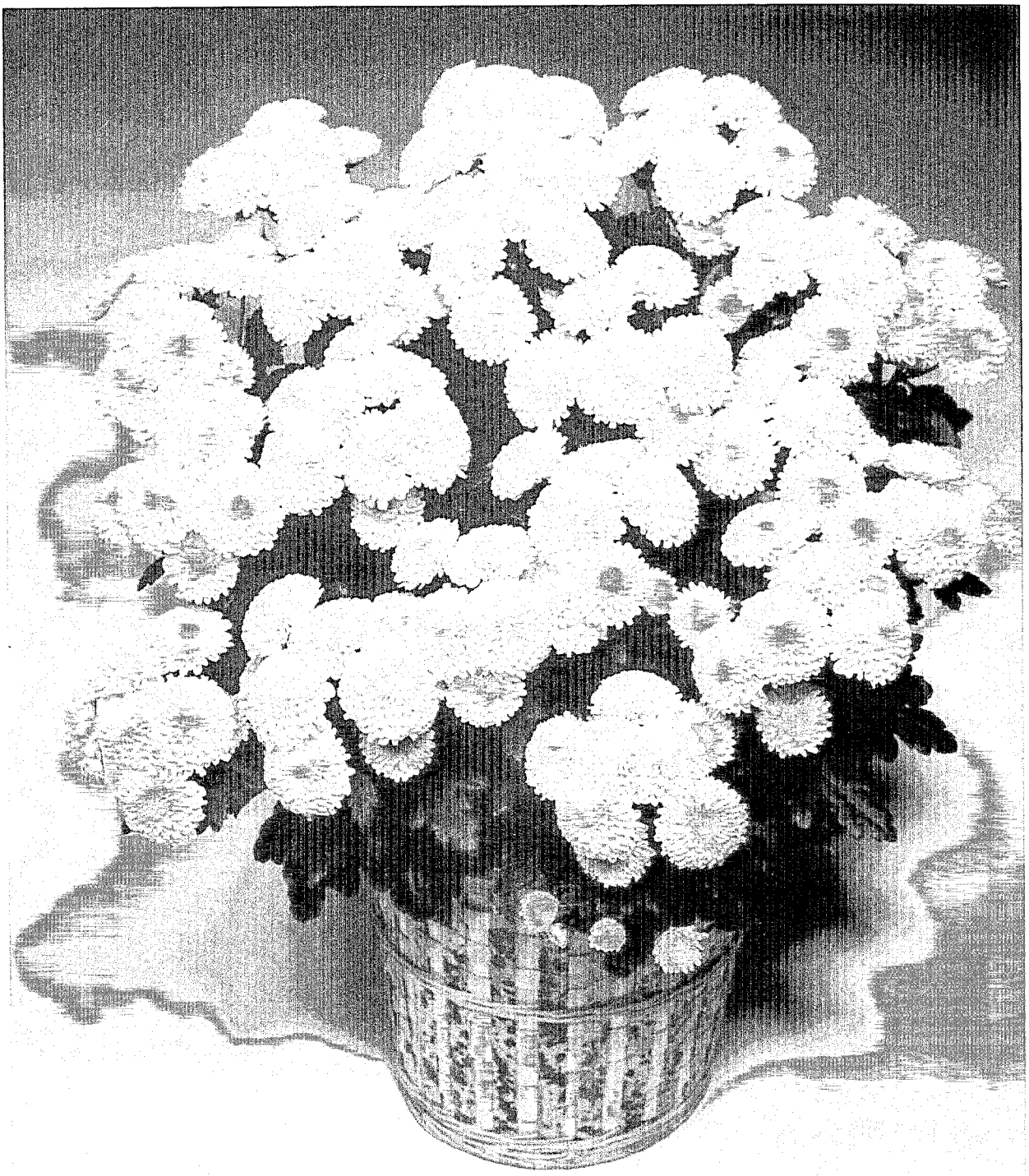

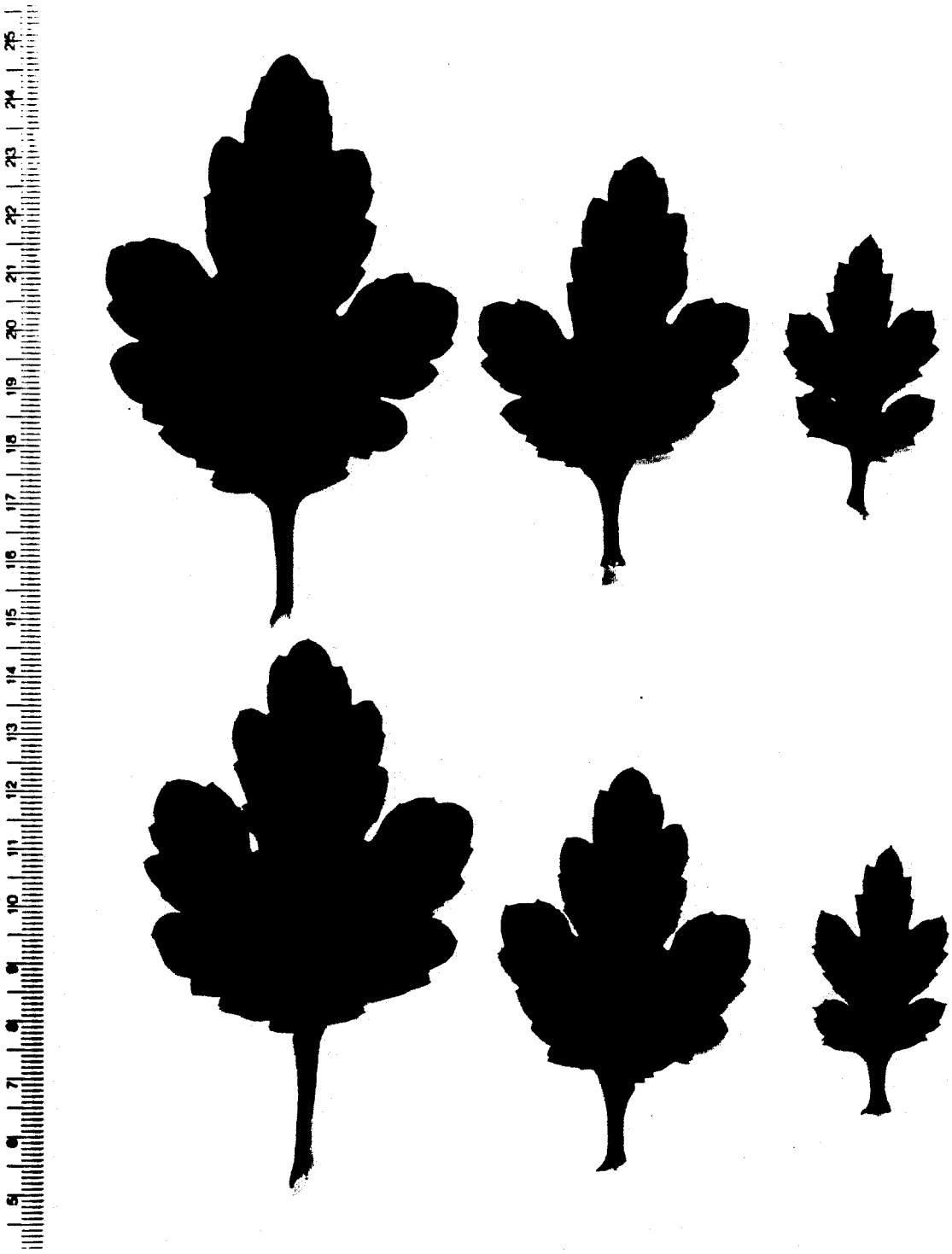

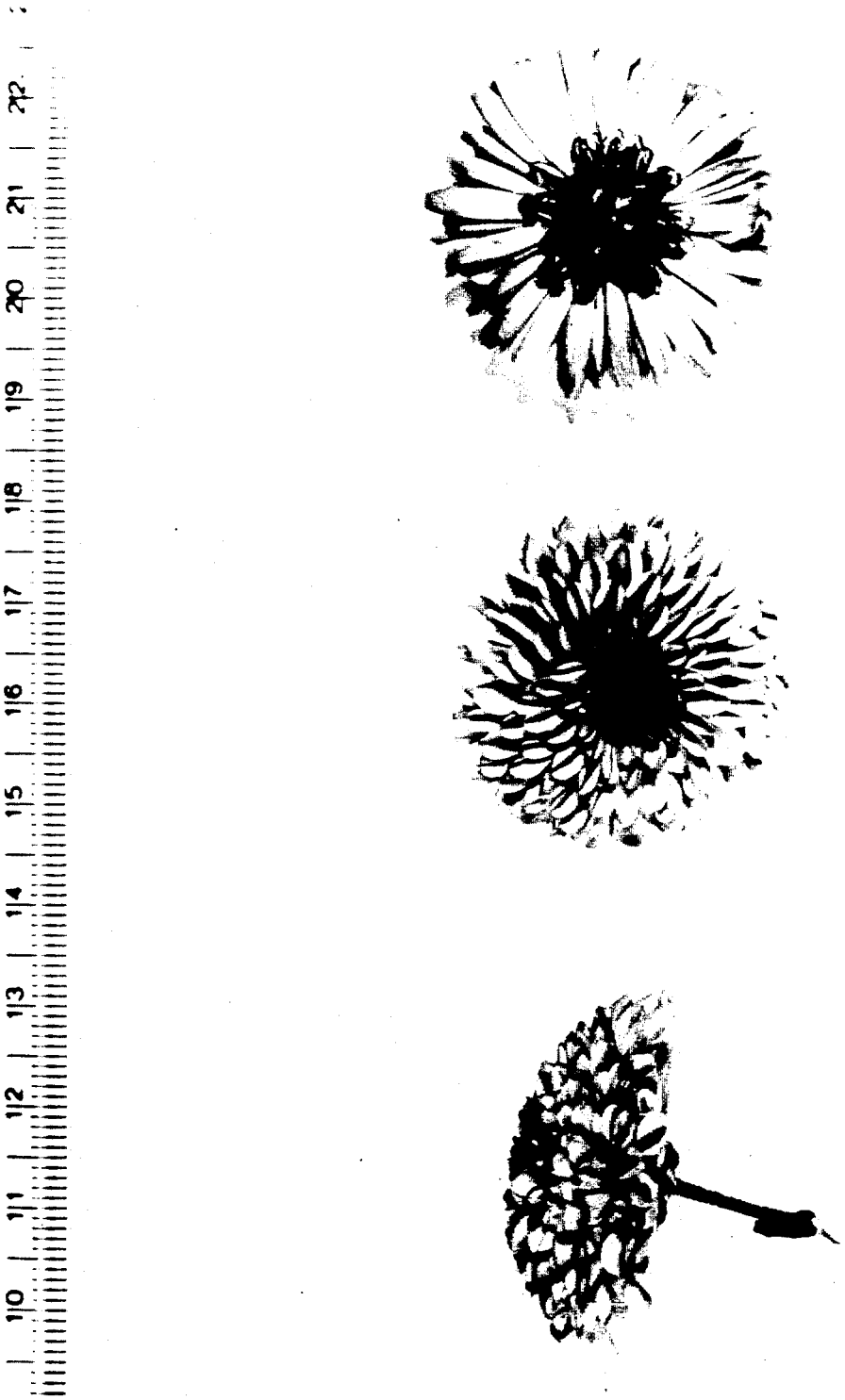
10
11
12
13
14
15
16
17
18
19
20
21
22